US006873123B2

(12) United States Patent
Marchand et al.

(10) Patent No.: US 6,873,123 B2
(45) Date of Patent: Mar. 29, 2005

(54) DEVICE AND METHOD FOR REGULATING INTENSITY OF BEAM EXTRACTED FROM A PARTICLE ACCELERATOR

(75) Inventors: Bruno Marchand, Nivelles (BE); Bertrand Bauvir, Liege (BE)

(73) Assignee: Ion Beam Applications S.A., Louvain-la-Neuve (BE)

( * ) Notice: Subject to any disclaimer, the term of this patent is extended or adjusted under 35 U.S.C. 154(b) by 0 days.

(21) Appl. No.: 10/479,380

(22) PCT Filed: Jun. 3, 2002

(86) PCT No.: PCT/BE02/00089

§ 371 (c)(1), (2), (4) Date: Nov. 25, 2003

(87) PCT Pub. No.: WO02/102123

PCT Pub. Date: Dec. 19, 2002

(65) Prior Publication Data

US 2004/0155206 A1 Aug. 12, 2004

(30) Foreign Application Priority Data

Jun. 8, 2001 (EP) ........................................... 01870122

(51) Int. Cl.[7] ............................ A61N 5/01; A61N 5/10; H05H 13/00

(52) U.S. Cl. .................. 315/502; 315/507; 315/111.61; 315/111.81; 250/505.1; 250/423 R; 250/424; 250/492.3; 250/492.1; 250/396 R

(58) Field of Search ................................ 315/502, 507, 315/111.61, 111.81; 250/505.1, 423 R, 424, 492.3, 492.1, 396 R

(56) References Cited

U.S. PATENT DOCUMENTS 6,717,162 B1 * 4/2004 Jongen .................... 250/505.1
6,736,831 B1 * 5/2004 Hartmann et al. ............. 607/1
6,745,072 B1 * 6/2004 Badura et al. ................. 607/2

FOREIGN PATENT DOCUMENTS

| | | |
|---|---|---|
| FR | 2 539 867 | 7/1984 |
| FR | 2 749 613 | 12/1997 |
| WO | WO 00/40064 | 7/2000 |

OTHER PUBLICATIONS

Vándoren, Vance J. "The Smith Predictor: A Process Engineer's Crystal Ball" Control Engineering May 1996, pp. 61–62.

* cited by examiner

*Primary Examiner*—Nikita Wells
(74) *Attorney, Agent, or Firm*—Merchant & Gould P.C.

(57) ABSTRACT

The invention concerns a device (10) for regulating the intensity of a beam extracted from a particle accelerator, such as a cyclotron, used for example for protontherapy, said particles being generated from an ion source. The invention is characterized in that it comprises at least: a comparator (90) determining a difference $\epsilon$ between a digital signal $I_R$ representing the intensity of the beam measured at the output of the accelerator and a setpoint value $I_C$ of the beam intensity: a Smith predictor (80) which determines on the basis of the difference $\epsilon$, a correct value of the intensity of the beam $I_P$; an inverted correspondence table (40) supplying, on the basis of the corrected value of the intensity of the beam $I_P$, a setpoint value $I_A$ for supply arc current from the ion source (20).

13 Claims, 4 Drawing Sheets

DEVICE AND METHOD FOR REGULATING INTENSITY OF BEAM EXTRACTED FROM A PARTICLE ACCELERATOR

SUBJECT OF THE INVENTION

The present invention concerns the technical field of regulating the intensity of a beam extracted from a particle accelerator.

The present invention relates to a device intended for rapidly and accurately regulating the intensity of a beam extracted from a particle accelerator, and more specifically a cyclotron.

The present invention also relates to a method for regulating the intensity of the beam extracted from a particle accelerator.

The present invention lastly relates to the use of this device or this method in proton therapy, and in particular in the technique of "Pencil Beam Scanning".

TECHNICAL BACKGROUND AND PRIOR ART

Cyclotrons are circular particle accelerators, which are used to accelerate positive or negative ions up to energies of a few MeV or more. This type of equipment is employed in various fields such as industry or medicine, more precisely in radiotherapy for the production of radioisotopes, or in proton therapy with a view to treating cancer tumors.

Cyclotrons generally comprise five main components: the ion source which generates the ionized particles, the device for vacuum confinement of the ionized particles, the electromagnet which produces the magnetic field that guides the ionized particles, the high-frequency accelerator system intended to accelerate the ionized particles, and the extraction device making it possible to deviate the ionized particles from their acceleration trajectory then remove them from the cyclotron in the form of a beam with a high kinetic energy. This beam is then directed at the target volume.

In the ion source of a cyclotron, the ions are obtained by ionizing a gas medium consisting of one or more gases in a closed compartment, by means of electrons accelerated strongly by cyclotron electron resonance under the effect of a high-frequency magnetic field injected into the compartment.

Such cyclotrons can be used in proton therapy. Proton therapy is intended to deliver a high dose in a well-defined target volume to be treated, while sparing the healthy tissue surrounding the volume in question. Compared with conventional radiotherapy (X-rays), protons have the advantage of delivering their dose at a precise depth which depends on the energy (Bragg peak). Several techniques for dispensing the dose in the target volume are known.

The technique developed by Pedroni and described in "The 200-MeV proton therapy project at the Paul Scherrer Institute: conceptual design and practical realization" MEDICAL PHYSICS, January 1995, USA, vol. 22, No. 1, pages 37–53, XP000505145 ISSN: 0094–2405, consists in dividing the target volume into elementary volumes known as "voxels". The beam is directed at a first voxel and, when the prescribed dose is reached, the irradiation is stopped by abruptly deviating the beam by means of a fast-kicking magnet. A scanning magnet is then controlled so as to direct the beam at a next voxel, and the beam is reintroduced so as to irradiate this next voxel. This process is repeated until all of the target volume has been irradiated. One of the drawbacks of this method is that the treatment time is long because of the successive stops and restarts of the beam between two voxels, and may be as much as several minutes, in typical applications.

Patent application WO00/40064 by the Applicant describes an improved technique, referred to as "pencil beam scanning", in which the beam does not have to be stopped between the irradiation of each individual voxel. The method described in this document consists in moving the beam continuously so as to "paint" the target volume layer by layer.

By simultaneously moving the beam and varying the intensity of this beam, the dose to be delivered to the target volume can be configured precisely. The intensity of the proton beam is regulated indirectly by altering the supply current of the ion source. To this end, a regulator is employed which makes it possible to regulate the intensity of the proton beam. This regulation, however, is not optimal.

Another technique used in proton therapy is the technique referred to as "Double Scattering". In this technique, the irradiation depth (i.e. the energy) is modulated with the aid of a wheel, referred to as a modulation wheel, rotating at a speed of the order 600 rpm. The absorbent parts of this modulator consist of an absorbent material, such as graphite or lexan. When these modulation wheels are manufactured, the depth modulation which is obtained is fairly close to predictions. The uniformity nevertheless remains outside the desired specifications. In order to achieve the specifications in respect of uniformity, rather than re-machining the modulation wheels it is less expensive to employ beam intensity regulation which is synchronized with the speed of rotation of the energy modulator. The modulation function is therefore established for each energy modulator, and is used as a trajectory which is provided as a setpoint to the beam intensity regulator. Rapid and accurate regulation of the intensity of the beam extracted from a particle accelerator is therefore also necessary in the double scattering techniques which use such a modulation wheel.

OBJECT OF THE INVENTION

It is an object of the present invention to provide a device and a method intended for regulating the intensity of a beam extracted from a particle accelerator, which does not have the drawbacks of the methods and devices of the prior art.

SUMMARY OF THE INVENTION

The present invention relates to a device for regulating the intensity of the beam extracted from a particle accelerator, such as a cyclotron, used for example for proton therapy, said particles being generated from an ion source, characterized in that it includes at least:

a comparator, which determines a difference between a digital signal representative of the beam intensity measured at the output of the accelerator and a setpoint value of the beam intensity;

a Smith predictor, which determines a corrected value of the beam intensity on the basis of said difference;

an inverted correspondence table, which provides a setpoint value for the supply of the arc current of the ion source on the basis of the corrected value of the beam intensity.

The device according to the invention may furthermore comprise an analog-digital converter, which converts the analog signal directly representative of the beam intensity measured at the output of the accelerator and provides a digital signal.

The device according to the invention will preferably furthermore comprise:

a lowpass filter, which filters said analog signal directly representative of the beam intensity measured at the output of the accelerator and provides a filtered analog signal;

a phase lead controller, which samples said filtered analog signal, compensates for the phase lag introduced by the lowpass filter and provides a digital signal to the comparator.

The device of the invention advantageously includes means for updating the content of the inverted correspondence table.

The sampling frequency is preferably between 100 kHz and 200 kHz, and the cutoff frequency of the lowpass filter is preferably between 2 and 6 kHz.

The present invention also relates to a method for regulating the intensity of the beam extracted from a particle accelerator, such as a cyclotron, used for example for proton therapy, said particles being generated from an ion source, by means of a digital regulation device operating at a given sampling frequency, characterized in that it comprises at least the following stages:

the beam intensity is measured at the output of the particle accelerator;

a digital signal representative of the measurement of the beam intensity is compared with the setpoint value of the beam intensity;

a corrected value of the beam intensity is determined by means of a Smith predictor;

a setpoint value for the supply of the arc current of the ion source is determined, on the basis of said corrected value of the beam intensity, by means of an inverted correspondence table.

In the method according to the invention, after the measurement of the beam intensity at the output of the particle accelerator, the analog signal directly representative of the measured beam intensity is preferably converted by means of an analog-digital converter in order to obtain a digital signal.

According to one embodiment of the method according to the invention, the analog signal directly representative of the measured beam intensity is filtered by means of a lowpass filter, giving a filtered analog signal;

the filtered analog signal is sampled, and the phase lag introduced by the filtering is compensated with the aid of a phase lead controller, in order to obtain a digital signal.

The correspondence between a value for the supply of the arc current of the ion source and a value of the beam intensity measured at the output of the accelerator is advantageously determined prior to the regulation.

In the correspondence between a value of the beam intensity measured at the output of the accelerator and a value for the supply of the arc current of the ion source, the values of the supply of the arc current corresponding to the beam intensity values higher than a limit are advantageously replaced by the supply value of the arc current corresponding to this limit.

The present invention lastly relates to the use of the device and the method of the invention in proton therapy, and in particular in the techniques of “Pencil Beam Scanning” and “double scattering”.

PROBLEMS ON WHICH THE PRESENT INVENTION IS BASED

The problems described below are encountered when using conventional regulation, for example PID, to carry out the technique referred to as “pencil beam scanning”, as described in the publication WO00/40064 by the Applicant.

Figure 1:
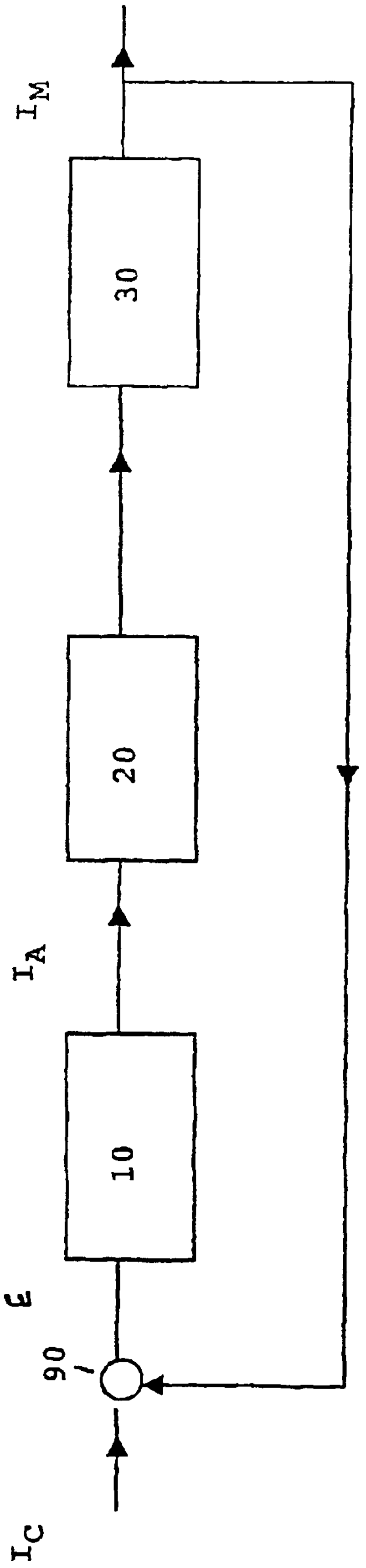
FIG. 1 represents a device for regulating the intensity of a beam extracted from a particle accelerator according to the prior art.

As shown by FIG. 1, a setpoint value $I_C$ of the beam intensity is provided to a conventional PID regulator 10, which determines a value $I_A$ of the arc current of the ion source 20. The beam intensity is measured by means of an ionization chamber 30, and the corresponding signal $I_M$ is compared with the setpoint value $I_C$ with the aid of a comparator 90, in order to provide an error signal $\epsilon$. According to the technique of continuous beam scanning, it is essential for the beam intensity to vary simultaneously with the movement, so as to obtain conformity of the delivered dose.

Figure 2:
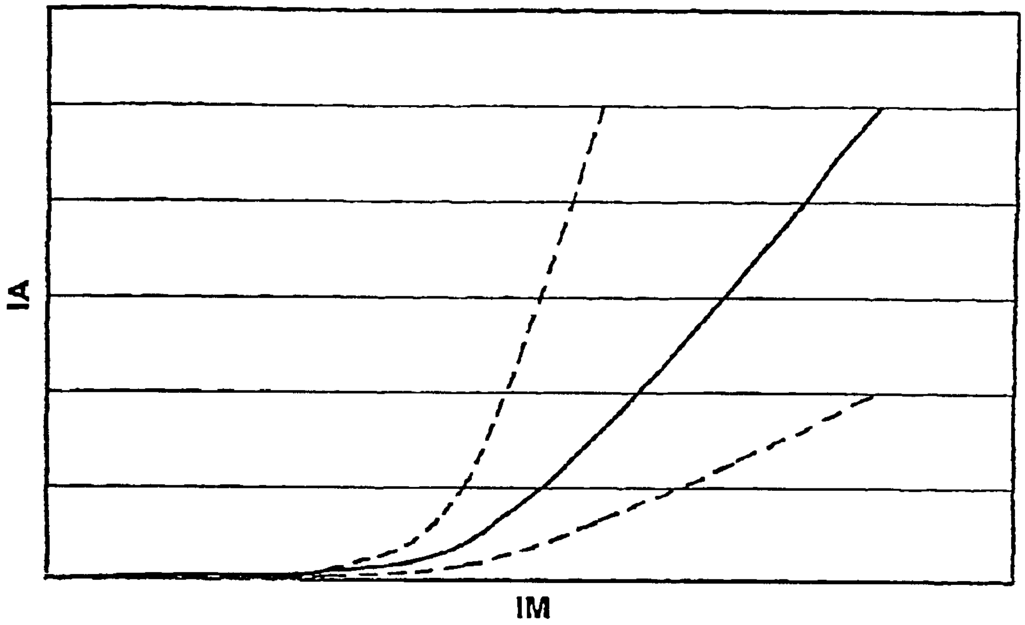
FIG. 2 represents the characteristic of the system, i.e. the correspondence between a value $I_A$ for the supply of the arc current of the ion source and a value $I_M$ of the beam intensity measured at the output of the accelerator.

Such a system has the following difficulties:

a significant pure dead time is due to the long transit time of a particle between its emission by the ion source 20 and its exit from the machine;

the characteristic of the system; which relates the intensity of the beam extracted from the particle accelerator $I_M$ to the strength of the arc current of the ion source $I_A$, is very nonlinear as shown by FIG. 2;

this characteristic may furthermore vary with time, as shown by the dashed curves in FIG. 2. This variation may take place rapidly because of the heating or cooling of the filament of the ion source when it is put into operation. It may also be due to the ageing of the filament. These two phenomena lead to variations of the characteristic with very different time constants;

the system is very noisy. The intensity of the beam generated by the ion source has significant noise, in particular at the sampling frequency which is used for the measurement.

The regulation of such a system by using the conventional regulation methods, such as the techniques of feedforward, feedback by proportional, integral and derivative action (PID) and cascade loops, was evaluated. Because of the significant pure dead time, all these methods give responses which either are too slow or are unstable. Nor do the conventional methods make it possible to address the problem of a system characteristic that fluctuates as a function of time, by using an average value of the characteristic over a given period, because the gain variations from one response to the other are in a very large ratio.

The variation of the characteristic depends on two phenomena which are very much decoupled: the first, with a short time constant, corresponds to the conditioning of the ion source, i.e. its temperature. Normal operation, continuous or intermittent with a high duty cycle, heats the ion source rapidly. This fast temperature establishment time might permit open-loop operation, i.e. without taking the actual characteristic of the system into account, by using conventional methods during the conditioning time. However, this compromise greatly limits the use of a conventional method with intermittent operation at a medium duty cycle, which often corresponds to the operating mode that is used.

The second phenomenon, with a longer time constant, is due to the ageing of the filament and the ion source itself. This slower change in the characteristic could therefore occasion the use of an average characteristic of the system. However, the use of an average characteristic leads to a regulation which either is too slow or is unstable.

It therefore seems clear that the conventional regulation methods cannot satisfactorily resolve the problems of regulating such a system, i.e. a pure dead time which is much longer than the main time constant of the system (about 4 times) and a variable nonlinear characteristic that requires an adaptive regulation method.

Rapid and accurate regulation of the intensity of the beam extracted from a particle accelerator is therefore confronted with many difficulties. However, such rapid and accurate regulation is important for using the "pencil beam scanning" technique.

DESCRIPTION OF A PREFERRED EMBODIMENT OF THE INVENTION

Figure 3:
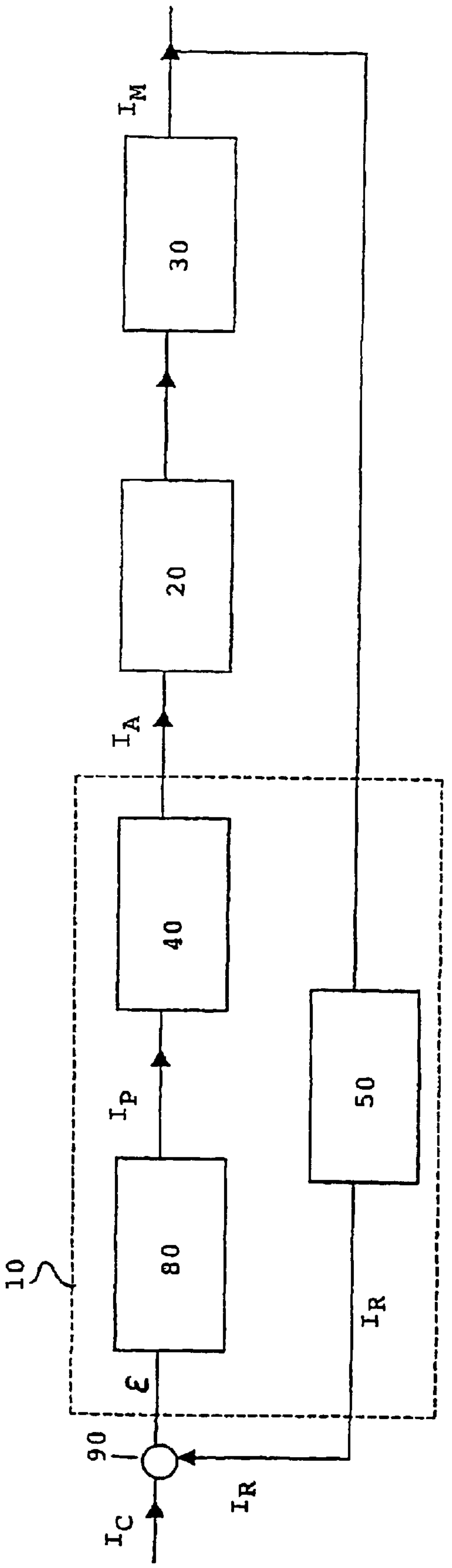
FIG. 3 represents one embodiment of a device for regulating the intensity of a beam extracted from a particle accelerator according to the invention.

The present invention consequently proposes to resolve this problem more specifically by using, according to a preferred embodiment, the regulation device 10 represented in FIG. 3 with the supply of the arc current of the ion source 20. The ion source produces an ion beam, which is accelerated during its transit through the accelerator, is extracted therefrom and passes through a device 30 for measuring the beam intensity at the output of the accelerator. This measuring device 30 may, for example, be an ionization chamber.

The regulator according to the invention was used for a cyclotron having the following exemplary and nonlimiting characteristics:

- fixed energy: 235 MeV
- pure dead time: 60 μsec. This pure dead time corresponds to the transit time of the ions through the accelerator. It therefore corresponds directly to the time required for measuring the effect of a modification of the setpoint of the arc current of the ion source on the intensity of the ion beam extracted from the machine.
- main time constant: 15 μs. This gives an indication of the time required for establishing the response of the system to a setpoint modification in an open loop.
- very nonlinear characteristic of the system, which leads to an open-loop characteristic corresponding substantially to that of a system with a hybrid dynamic response (all or nothing).
- variation of the characteristic with time.
- very noisy measured signal. This is because the ion source is unstable, which leads to a very high noise level for the intensity of the beam after extraction. The observed noise/signal ratio is of the order of 150%. For a digital embodiment of the regulator, the adopted sampling frequencies therefore lead to a very low signal/noise ratio.

In the regulation device of the invention, which is represented in FIG. 3, the following stages are carried out:

- the setpoint value of the beam intensity $I_C$ is provided in the form of a 0–10 V analog signal (10 V corresponding to a beam intensity of 300 nA);
- the beam intensity is measured by means of an ionization chamber 30, and the measurement $I_M$ is provided to the regulation device 10 by means of a 0–15 μA analog signal (15 μA corresponding to a beam intensity of 300 nA);
- this analog signal $I_M$ is converted into a digital signal $I_R$ by a converter 50;
- this signal $I_R$ is compared with the setpoint $I_C$ by the comparator in order to provide an error signal $\epsilon$;
- this error signal $\epsilon$ is provided to the regulator 80 of the "Smith predictor" type;
- the output $I_P$ of the Smith predictor 80 is then provided to the input of an inverted correspondence table 40. The correspondence table 40 numerically provides the nonlinear relation between the arc current of the ion source $I_A$ and the intensity of the ion beam $I_M$ extracted from the accelerator. It therefore makes it possible to identify the nonlinear characteristic of the system. The output of the inverted correspondence table is converted into an analog signal of the 4–20 mA type $I_A$, which is provided by the regulation device 10 as a value of the setpoint for the supply of the arc current of the ion source.

Figure 4:
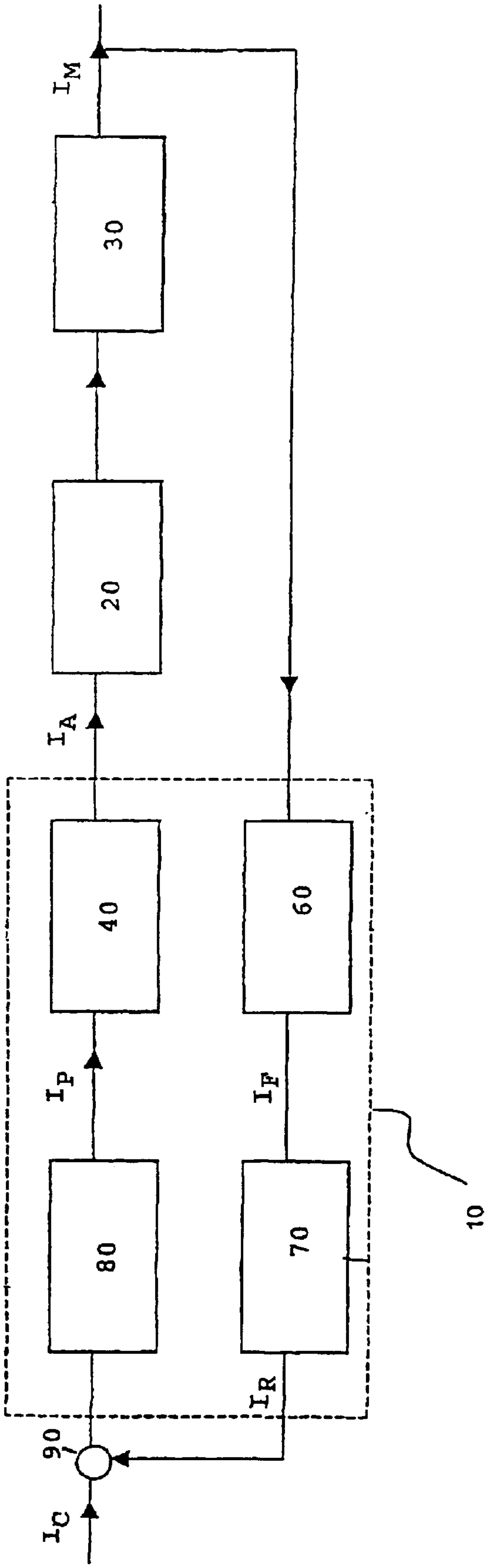
FIG. 4 represents a second embodiment of a device for regulating the intensity of a beam extracted from a particle accelerator according to the invention.

Simulations show that such a device allows good regulation. It is, however, sensitive to low-frequency perturbations. In order to resolve this problem, a preferred variant of the device according to the invention has been developed, which is represented in FIG. 4. In this device 10, a lowpass filter 60 and a phase lead controller 70 are introduced into the feedback. The filter 60 is, for example, a first-order lowpass filter. The cutoff frequency is 4.5 kHz. In order to compensate for the phase lag introduced by the filter, a phase lead controller 70 is used (filtered derivator) which compensates for this phase shift.

Both the device in FIG. 3 and the one in FIG. 4 have an inverted correspondence table 40. The content of this table 40 is determined prior to each use of the device, in the following way:

- since the regulator is in an open loop, the setpoint of the arc current of the ion source 20 is increased progressively from 0 to 20 mA in the form of a 100 ms ramp;
- the beam intensity is measured for each of the 4000 sampled points;
- the table which is obtained is inverted, so as to provide a corresponding value of the arc current of the ion source $I_A$ as a function of the beam intensity $I_M$.

This inverted table is loaded into the regulation device 10.

In practice, this operation is carried out twelve or so times in succession. This makes it possible to ensure that the parameters reach a plateau corresponding to the steady-state temperature of the filament. In order to eliminate the noise, an average of the last 4 tables is calculated. These operations, which are carried out automatically, last at most 1.5 s. In a variant of the invention, the values of $I_A$ corresponding to the values of $I_M$ higher than a given limit are replaced by the value of $I_A$ corresponding to this limit. The curves in FIG. 2 are therefore clipped. This is a safety element making it possible to guarantee that the intensity of the beam produced by the accelerator will never be more than this limit.

The device according to the invention is produced by means of an electronics board which employs digital technology of the DSP type (Digital Signal Processing).

The synthesis of the Smith predictor was carried out in the Laplace domain, and the discretization is provided by the Z transform using the method of pole-zero correspondence. over-sampling might have been adequate to avoid any problem associated with the discretization, but current DSP technology did not allow us to go beyond 100 kHz.

The regulation method according to the present invention has several advantages. First, it allows controlled adaptation, i.e. it requires a very short computation time compared with modern adaptive control methods and allows a very straightforward structural change since the identification is carried out by constructing a correspondence table, which is then sufficient to invert numerically in order to linearize the characteristic of the system seen by the main regulator.

It furthermore offers significant flexibility since it could be employed for accurate, reproducible, robust and high-performance regulation of any ion source with which a cyclotron is equipped, and especially through the advantage of adaptive-type regulation allowing re-identification of the characteristic of the system when this varies with time. It therefore allows the identification and regulation of an accelerator other than the C235 cyclotron for which this regulation was originally developed.

What is claimed is:

1. A device (10) for regulating the intensity of the beam extracted from a particle accelerator, such as a cyclotron, used for example for proton therapy, said particles being generated from an ion source, characterized in that it includes at least:

a comparator (90), which determines a difference $\epsilon$ between a digital signal $I_R$ representative of the beam intensity measured at the output of the accelerator and a setpoint value of the beam intensity $I_C$;

a Smith predictor (80), which determines a corrected value of the beam intensity $I_P$ on the basis of the difference $\epsilon$;

an inverted correspondence table (40), which provides a setpoint value $I_A$ for the supply of the arc current of the ion source (20) on the basis of the corrected value of the beam intensity $I_P$.

2. The device as claimed in claim 1, characterized in that it furthermore comprises an analog-digital converter (50), which converts the analog signal $I_M$ directly representative of the beam intensity measured at the output of the accelerator and provides a digital signal $I_R$.

3. The device as claimed in claim 1, characterized in that it furthermore comprises:

a lowpass filter (60), which filters the analog signal $I_M$ directly representative of the beam intensity measured at the output of the accelerator and provides a filtered analog signal $I_F$;

a phase lead controller (70), which samples the filtered analog signal $I^F$, compensates for the phase lag introduced by the lowpass filter (60) and provides a digital signal $I_R$ to the comparator (90).

4. The device as claimed in claim 1, characterized in that it includes means for updating the content of the inverted correspondence table (40).

5. The device as claimed in claim 1, characterized in that the sampling frequency is between 100 kHz and 200 kHz.

6. The device as claimed in claim 1, characterized in that the cutoff frequency of the lowpass filter (60) is between 2 and 6 kHz.

7. Use of the device as claimed in claim 1 in proton therapy, and in particular in the techniques of "Pencil Beam Scanning" and "double scattering".

8. A method for regulating the intensity of the beam extracted from a particle accelerator, such as a cyclotron, used for example for proton therapy, said particles being generated from an ion source (20), by means of a digital regulation device (10) operating at a given sampling frequency, characterized in that it comprises at least the following stages:

the beam intensity ($I_M$) is measured at the output of the particle accelerator;

a digital signal $I_R$ representative of the measurement of the beam intensity ($I_M$) is compared with the setpoint value $I_C$ of the beam intensity, by means of a comparator (90);

a corrected value of the beam intensity $I_P$ is determined by means of a Smith predictor (80);

a setpoint value $I_A$ for the supply of the arc current of the ion source (20) is determined, on the basis of the corrected value $I_P$ of the beam intensity, by means of an inverted correspondence table (40).

9. The regulation method as claimed in claim 8, characterized in that, after the measurement of the beam intensity at the output of the particle accelerator, the analog signal $I_M$ directly representative of the measured beam intensity is converted by means of an analog-digital converter (50) in order to obtain a digital signal $I_R$.

10. The method as claimed in claim 8, characterized in that after the measurement of the beam intensity at the output of the particle accelerator:

the analog signal $I_M$ directly representative of the measured beam intensity is filtered by means of a lowpass filter (60), giving a filtered analog signal $I_F$;

the filtered analog signal $I_F$ is sampled, and the phase lag introduced by the filtering is compensated with the aid of a phase lead controller (70), in order to obtain a digital signal $I_R$.

11. The method as claimed in claim 8, characterized in that the correspondence between a value $I_A$ for the supply of the arc current of the ion source (20) and a value $I_M$ of the beam intensity measured at the output of the accelerator is determined prior to the regulation.

12. The method as claimed in claim 8, characterized in that, in the correspondence between a value $I_M$ of the beam intensity measured at the output of the accelerator and a value $I_A$ for the supply of the arc current of the ion source, the values of $I_A$ corresponding to the values of $I_M$ higher than a limit are replaced by the value of $I_A$ corresponding to this limit.

13. Use of the method of as claimed in claim 7 in proton therapy, and in particular in the techniques of "Pencil Beam Scanning" and "double scattering".

* * * * *